(12) United States Patent
Schneider et al.

(10) Patent No.: US 8,007,614 B2
(45) Date of Patent: Aug. 30, 2011

(54) ELASTOMERIC NONWOVEN LAMINATES AND PROCESS FOR PRODUCING SAME

(75) Inventors: Uwe Schneider, Mason, OH (US); Donald Carroll Roe, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 12/869,999

(22) Filed: Aug. 27, 2010

(65) Prior Publication Data

US 2011/0030883 A1 Feb. 10, 2011

Related U.S. Application Data

(63) Continuation of application No. 10/915,239, filed on Aug. 10, 2004, now abandoned.

(51) Int. Cl.
*B32B 38/00* (2006.01)
*B32B 37/02* (2006.01)

(52) U.S. Cl. .......... 156/163; 156/60; 156/160; 156/227; 156/229; 156/268; 428/98; 428/105; 428/107; 428/108; 428/114; 428/188; 442/329; 604/385.04; 604/385.24; 604/385.27

(58) Field of Classification Search .................. 428/105, 428/114, 188, 98, 107, 108; 442/329; 604/385.27, 604/385.24, 385.04; 156/60, 160, 227, 229, 156/268
See application file for complete search history.

(56) References Cited

U.S. PATENT DOCUMENTS

| | | |
|---|---|---|
| 3,468,748 A | 9/1969 | Bassett |
| 3,575,782 A | 4/1971 | Hansen |
| 3,848,594 A | 11/1974 | Buell |
| 3,860,003 A | 1/1975 | Buell |
| 4,223,059 A | 9/1980 | Schwarz |
| 4,381,781 A | 5/1983 | Sciaraffa |
| 4,443,511 A | 4/1984 | Worden et al. |
| 4,454,184 A | 6/1984 | Britton |
| 4,525,407 A | 6/1985 | Ness |
| 4,610,678 A | 9/1986 | Weisman |
| 4,662,875 A | 5/1987 | Hirotsu |
| 4,673,402 A | 6/1987 | Weisman |
| 4,695,278 A | 9/1987 | Lawson |
| 4,699,622 A | 10/1987 | Toussant |
| 4,720,415 A | 1/1988 | Vander Wielen et al. |
| 4,795,454 A | 1/1989 | Dragoo |

(Continued)

FOREIGN PATENT DOCUMENTS

EP 0 631 767 A1 1/1995

(Continued)

OTHER PUBLICATIONS

PCT International Search Report, Mailed Feb. 1, 2006, 5 pages.

*Primary Examiner* — Brent T O'Hern
(74) *Attorney, Agent, or Firm* — Charles R. Matson

(57) ABSTRACT

An elastomeric laminate for use in an absorbent article can have a first plurality of elastomeric strands and a second plurality of elastomeric strands bonded to a first substrate. The first plurality of elastomeric strands can be bonded to the first substrate in a first orientation while the second plurality of elastomeric strands is joined to the first substrate in a second orientation. The first and second orientations can be different such that the elastomeric laminate can accommodate tension forces which act on the laminate from different axes. Optionally, a second substrate or a third plurality of elastomeric strands may be added to the elastomeric laminate.

17 Claims, 12 Drawing Sheets

U.S. PATENT DOCUMENTS

| | | |
|---|---|---|
| 4,808,178 A | 2/1989 | Aziz |
| 4,834,735 A | 5/1989 | Alemany |
| 4,846,815 A | 7/1989 | Scripps |
| 4,857,067 A | 8/1989 | Wood |
| 4,861,652 A | 8/1989 | Lippert et al. |
| 4,888,231 A | 12/1989 | Angstadt |
| 4,894,060 A | 1/1990 | Nestegard |
| 4,909,803 A | 3/1990 | Aziz |
| 4,938,753 A | 7/1990 | Van Gompel |
| 4,940,464 A | 7/1990 | Van Gompel |
| 4,946,527 A | 8/1990 | Battrell |
| 4,963,140 A | 10/1990 | Robertson |
| 4,968,312 A | 11/1990 | Khan |
| 4,990,147 A | 2/1991 | Freeland |
| 5,062,840 A | 11/1991 | Holt |
| 5,092,861 A | 3/1992 | Nomura |
| 5,137,537 A | 8/1992 | Herron |
| 5,143,679 A | 9/1992 | Weber et al. |
| 5,147,345 A | 9/1992 | Young |
| 5,151,092 A | 9/1992 | Buell |
| 5,156,793 A | 10/1992 | Buell et al. |
| 5,167,897 A | 12/1992 | Weber et al. |
| 5,171,236 A | 12/1992 | Dreier |
| 5,221,274 A | 6/1993 | Buell |
| 5,242,436 A | 9/1993 | Weil |
| 5,246,433 A | 9/1993 | Hasse |
| 5,260,345 A | 11/1993 | Desmarais |
| 5,269,775 A | 12/1993 | Freeland |
| 5,306,266 A | 4/1994 | Freeland |
| 5,342,338 A | 8/1994 | Roe |
| 5,385,775 A | 1/1995 | Wright |
| 5,387,207 A | 2/1995 | Dyer |
| 5,397,318 A | 3/1995 | Dreier |
| 5,499,978 A | 3/1996 | Buell |
| 5,507,736 A | 4/1996 | Clear |
| 5,514,121 A | 5/1996 | Roe |
| 5,540,671 A | 7/1996 | Dreier |
| 5,554,142 A | 9/1996 | Dreier |
| 5,554,145 A | 9/1996 | Roe |
| 5,569,234 A | 10/1996 | Buell |
| 5,571,096 A | 11/1996 | Dobrin |
| 5,580,411 A | 12/1996 | Nease |
| 5,591,152 A | 1/1997 | Buell |
| 5,634,917 A | 6/1997 | Fujioka et al. |
| 5,650,222 A | 7/1997 | DesMarais et al. |
| 5,653,703 A | 8/1997 | Roe |
| 5,669,897 A | 9/1997 | Lavon |
| 5,669,996 A | 9/1997 | Jessup |
| 5,693,165 A | 12/1997 | Schmitz |
| 5,865,823 A | 2/1999 | Curro |
| 5,897,545 A | 4/1999 | Kline |
| 5,928,211 A | 7/1999 | Gustafsson et al. |
| 5,938,648 A | 8/1999 | Lavon |
| 5,941,864 A | 8/1999 | Roe |
| 5,947,947 A | 9/1999 | Tanzer et al. |
| 5,957,908 A | 9/1999 | Kline |
| 5,977,430 A | 11/1999 | Roe |
| 5,997,520 A | 12/1999 | Ahr |
| 6,004,306 A | 12/1999 | Robles |
| 6,010,490 A | 1/2000 | Freeland |
| 6,013,063 A | 1/2000 | Roe |
| 6,093,663 A | 7/2000 | Ouellette et al. |
| 6,120,487 A | 9/2000 | Ashton |
| 6,120,489 A | 9/2000 | Johnson |
| 6,168,584 B1 | 1/2001 | Allen |
| 6,179,820 B1 | 1/2001 | Fernfors |
| 6,187,696 B1 | 2/2001 | Lim |
| 6,248,851 B1 | 6/2001 | Maugans et al. |
| 6,290,979 B1 | 9/2001 | Roe et al. |
| 6,432,098 B1 | 8/2002 | Kline |
| 6,878,647 B1 | 4/2005 | Rezai et al. |
| 2003/0088226 A1 | 5/2003 | Takagi et al. |
| 2003/0091807 A1 | 5/2003 | Desai et al. |
| 2003/0233082 A1 | 12/2003 | Kline et al. |
| 2004/0193133 A1 | 9/2004 | Desai et al. |
| 2005/0027279 A1 | 2/2005 | Minato et al. |

FOREIGN PATENT DOCUMENTS

| | | |
|---|---|---|
| EP | 0 847 738 A1 | 6/1998 |
| EP | 0 847 738 B1 | 4/2002 |
| EP | 1 197 195 A1 | 4/2002 |
| EP | 0 985 394 B1 | 9/2002 |
| JP | 2002-192641 A | 7/2002 |
| WO | WO 00/37000 A1 | 6/2000 |
| WO | WO 01/39709 A1 | 6/2001 |
| WO | WO 01/87589 A2 | 11/2001 |
| WO | WO 01/88245 A2 | 11/2001 |

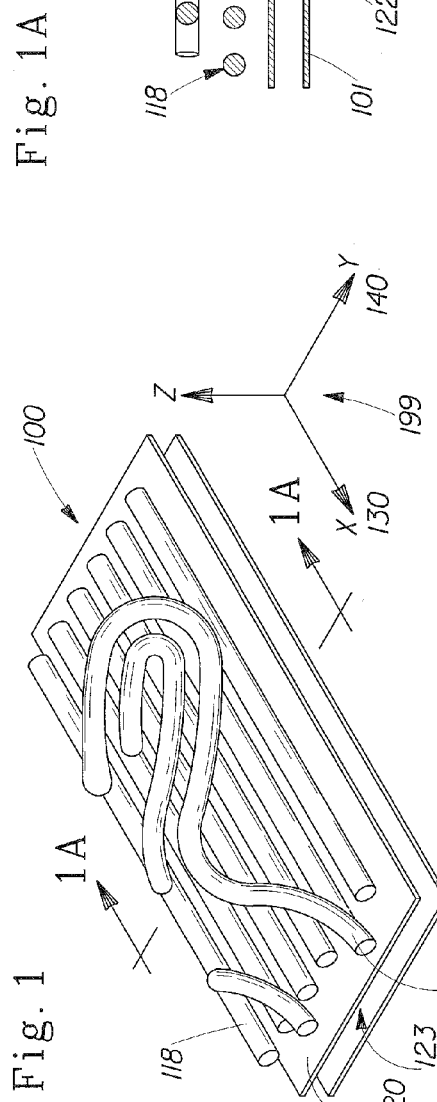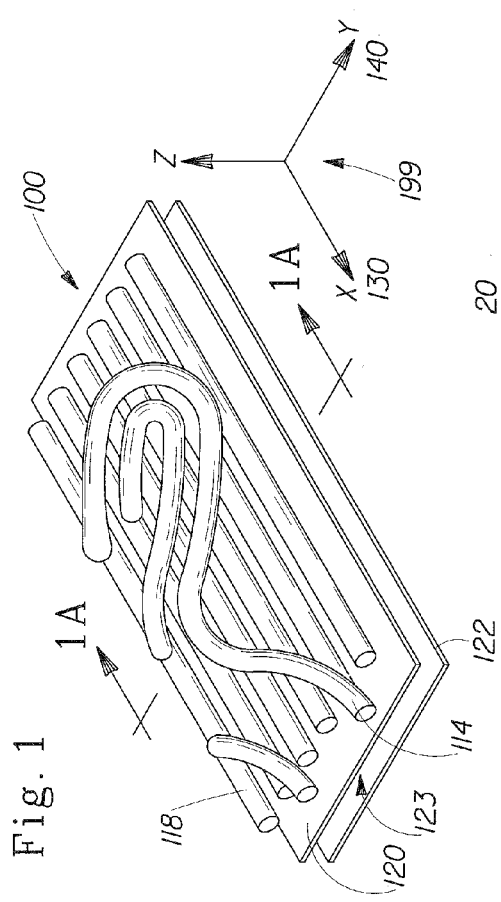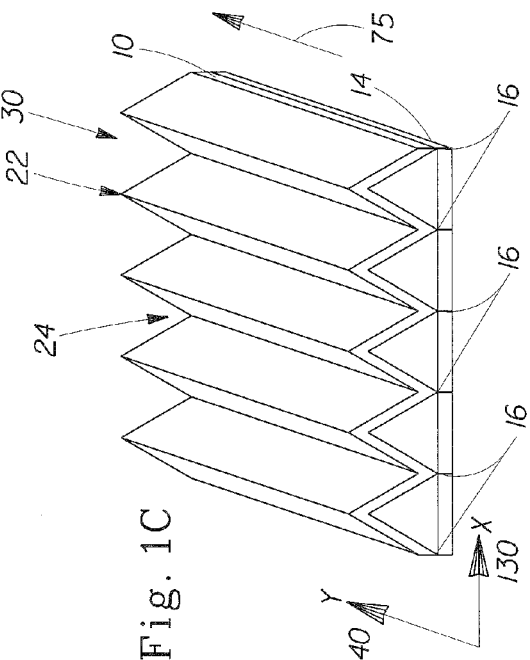

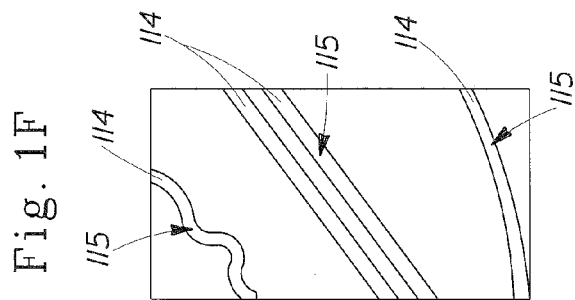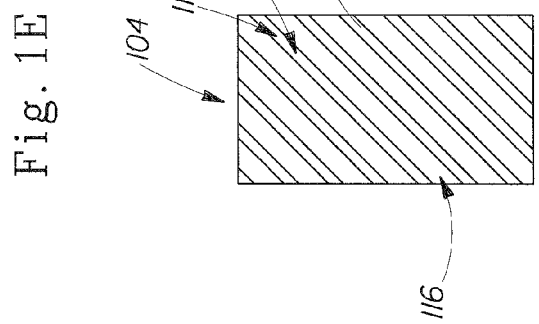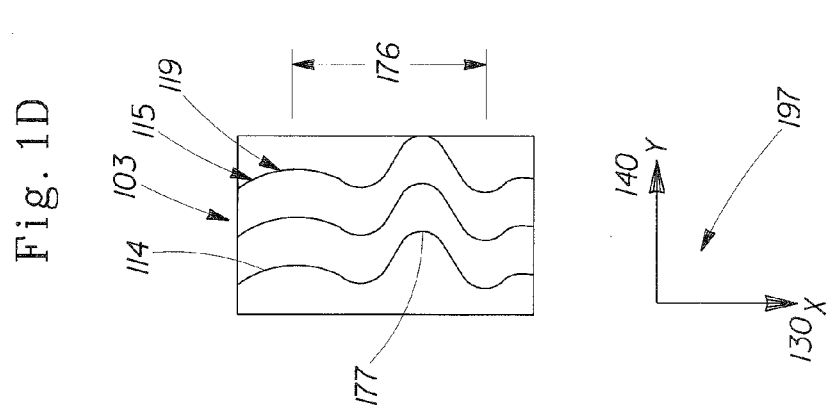

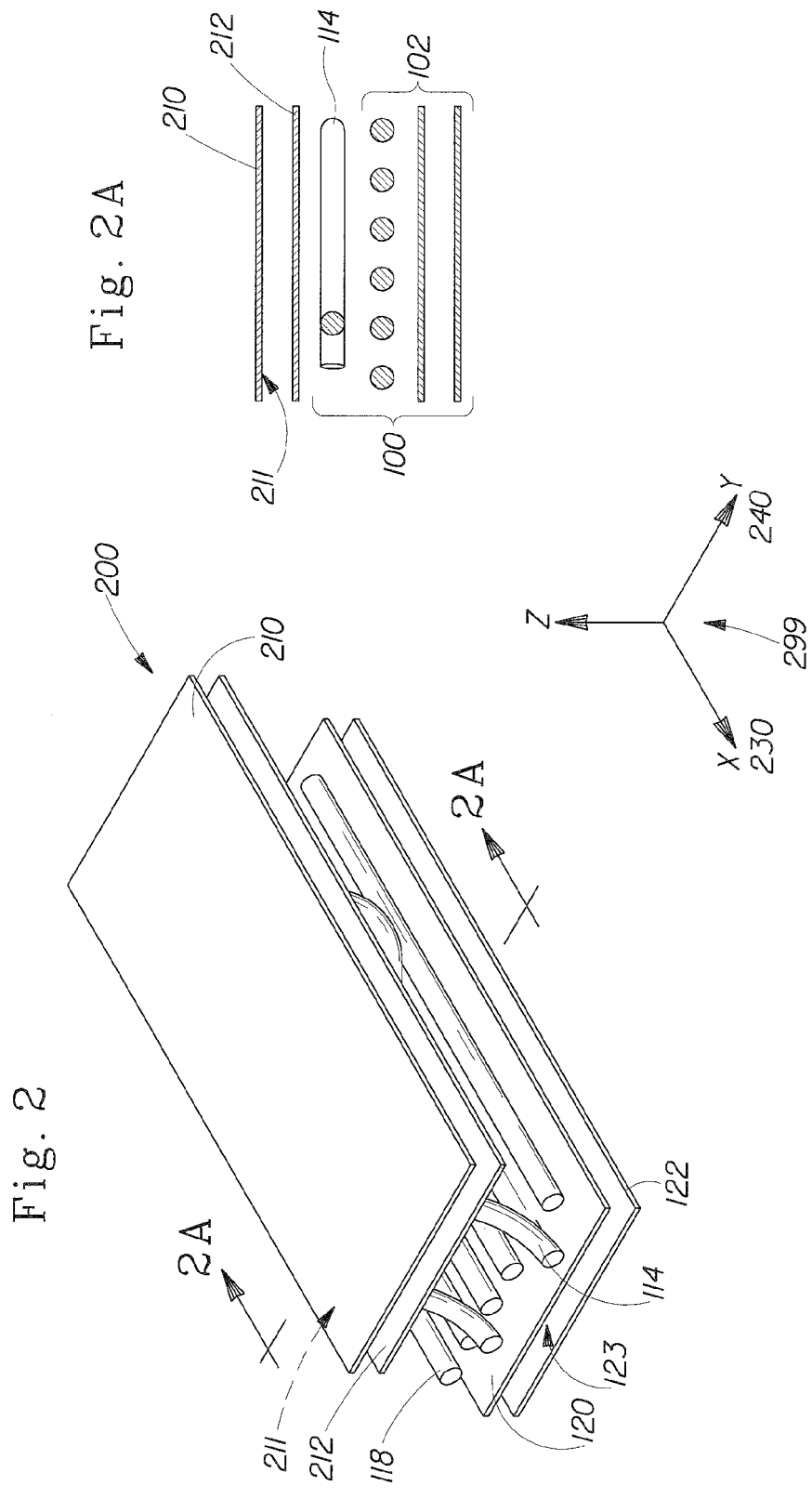

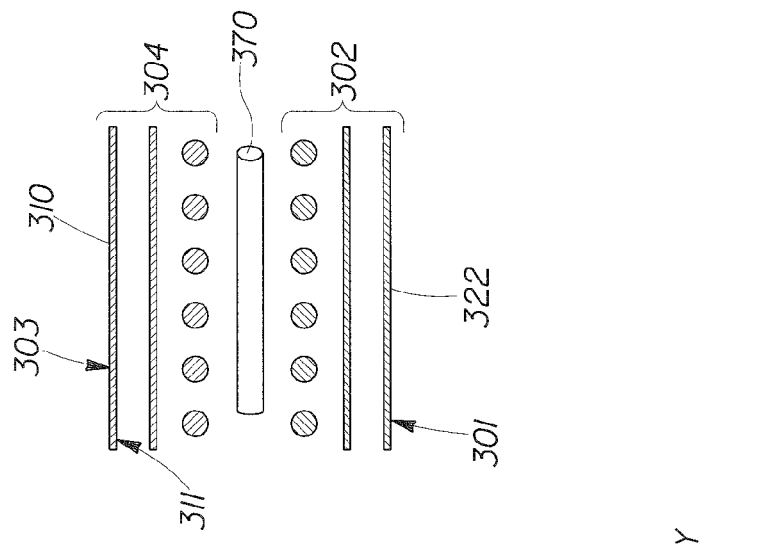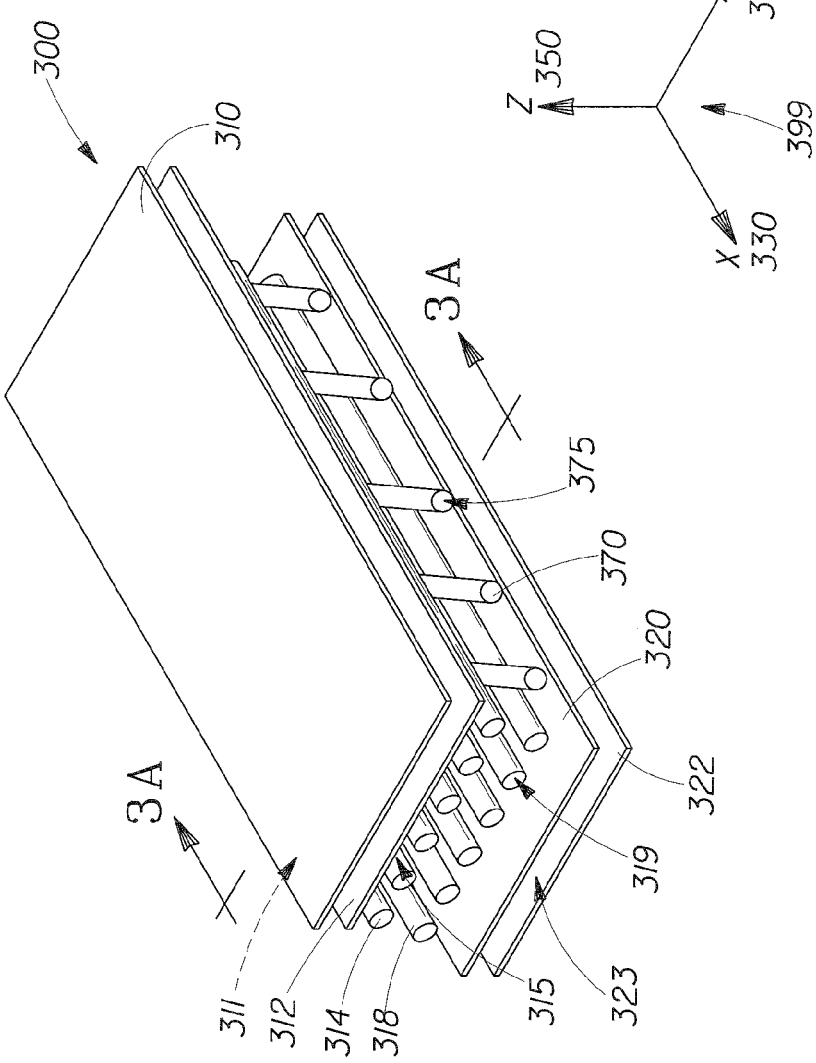

ELASTOMERIC NONWOVEN LAMINATES AND PROCESS FOR PRODUCING SAME

CROSS REFERENCE TO RELATED APPLICATION

This application is a continuation of U.S. application Ser. No. 10/915,239 filed Aug. 10, 2004 now abandoned, which is incorporated by reference herein.

FIELD OF THE INVENTION

The present invention relates to an elastomeric laminate of a strand elastic and a substrate. The elastomeric laminate may be used in a variety of articles and is particularly useful in disposable absorbent articles such as baby diapers, adult incontinence articles, feminine hygiene articles, baby swim diapers, bibs, wound dressings, and any other articles where a cost effective stretchable material may be desirable. The present invention also relates to a method and apparatus for manufacturing the elastomeric laminate.

BACKGROUND

Elastomeric nonwoven laminates are used in a wide variety of applications including extensive use in absorbent articles. For example, such laminates have been used in the topsheet, backsheet, waistband, and fastening elements of absorbent articles. Typical elastomeric nonwoven laminates comprise a layer of nonwoven and a layer of elastic. The layer of nonwoven can provide a feel of softness to a wearer of the absorbent article and may protect a wearer's skin from abrasion caused by the extension and contraction of the elastic.

Elastomeric nonwoven laminates in an absorbent article are subjected to many different forces. For example, in a waistband application, a tension force can be applied to the elastomeric nonwoven laminate such that the waistband is stretched from its non-stretched state to a stretched state. In reaction to the tension force, the waistband provides a contracting force in the opposite direction of the tension force. Specifically, the elastic layer wants to contract to a lower energy state, i.e. a non-stretched state instead of being in a stretched state. The contracting force in turn creates a normal force which acts against a waist of a wearer. The normal force, which is proportional to the contracting force, holds the absorbent article in place about the waist of the wearer. Also, the weight of the absorbent article provides a sagging tension force which tends to pull the absorbent article downward. These sagging tension forces are increased with the retention of body exudates by the absorbent article.

In general, the tension force provided acts in a primary direction of extensibility of the elastomeric nonwoven laminate. The primary direction of extensibility depends greatly on the orientation of the elastic layer and the way in which the elastic layer was bonded to the nonwoven. Typically, the primary direction of extensibility is parallel to a longitudinal axis of the elastomeric nonwoven laminate. In the primary direction of extensibility, the elastomeric nonwoven laminate has the greatest amount of elastic extensibility.

Contrarily, the sagging tension forces act in a direction which is not parallel to the primary direction of extensibility. Instead, the sagging tension forces tend to act more along a secondary direction of extensibility. Because the nonwoven of the elastomeric nonwoven laminate is elastically extensible to a small degree, the elastomeric nonwoven laminate is also elastically extensible in the secondary direction of extensibility. However, because the elastomeric nonwoven is not necessarily intended to be extensible in the secondary direction of extensibility, the elastomeric nonwoven laminate generally has a higher modulus of elasticity (resistance to stretching) in the secondary direction of extensibility than the primary direction of extensibility.

Under initial loading conditions, i.e. fit when the absorbent article is dry, the contracting three exerted by the elastic layer of the waistband creates a sufficient normal force to hold the absorbent article about the waist of the wearer and thereby overcome the sagging tension forces exerted by the unloaded absorbent article. In addition, the nonwoven of the elastomeric nonwoven laminate generally has a modulus of elasticity in the secondary direction of extensibility which is high enough to overcome the sagging tension forces of an unloaded absorbent article.

In contrast, once the absorbent article takes on body exudates and becomes loaded, the sagging tension forces, which are exerted on the waistband and are not in the primary direction of extensibility, are increased. These sagging tension forces may overcome the normal force exerted on the waist of the wearer. Thus, the normal force may not be sufficient to prevent the absorbent article from sagging/slumping on the waist of the wearer. Also, these sagging tension forces, can also overcome the modulus of elasticity of the nonwoven of the elastomeric nonwoven laminate such that the nonwoven is extended in the secondary direction of extensibility. This extension of the nonwoven in the secondary direction of extensibility can exacerbate the sagging slumping effect of the absorbent article on the waist of the wearer.

Also exacerbating this problem is the fact that a wearer's body is contoured. Because a wearer's body is contoured, the forces that are exerted on a nonwoven laminate may not necessarily be distributed evenly across the nonwoven laminate. Thus, the elastomeric nonwoven laminate may experience higher forces on one side of the elastomeric nonwoven laminate and lower forces on another side.

Consequently, it would be beneficial to provide a cost effective elastomeric laminate that can accommodate the tension forces and the sagging tension forces of a loaded absorbent article. Moreover, it would be beneficial to provide an elastomeric laminate that can also better accommodate the contours of a wearer's body. Also, it would be beneficial to provide a method and apparatus for making such a material.

SUMMARY OF THE INVENTION

In order to solve one or more of the problems found in the art, an elastomeric laminate and a method of producing the same is provided. The elastomeric laminates discussed herein may be incorporated into many different regions of absorbent articles. An elastomeric laminate comprising an extensible intermediate laminate and a second plurality of elastomeric strands is described herein. The extensible intermediate laminate comprises a first substrate having a bonding surface and a face opposite the bonding surface. A first plurality of elastomeric strands is bonded to the bonding surface of the first substrate along a first orientation. The second plurality of elastomeric strands is bonded to the extensible intermediate laminate along a second orientation wherein the first orientation is different from and non-orthogonal to the second orientation. The second plurality of elastomeric strands is joined to the face or the bonding surface of the first substrate.

Another embodiment comprises a first extensible intermediate laminate, a second extensible intermediate laminate, and a third plurality of elastomeric strands. The first extensible intermediate laminate comprises a first substrate having a first bonding surface and a first face opposite the first bonding surface. A first plurality of elastomeric strands extending along a first orientation is bonded to the first bonding surface of the first substrate.

The second extensible intermediate laminate comprises a second substrate which has a second bonding surface and a second face opposite the second bonding surface. A second plurality of elastomeric strands extending along a second orientation is bonded to the second bonding surface of the second substrate. In addition, the first extensible intermediate laminate and the second extensible intermediate laminate are joined in a face to face orientation.

The third plurality of elastomeric strands extends along a third orientation which is different from the first orientation and the second orientation. The third plurality of elastomeric strands is bonded to at least one of the first face, the first bonding surface of the first extensible intermediate laminate, the second face, and the second bonding surface of the second extensible intermediate laminate.

BRIEF DESCRIPTION SHOWN IN THE DRAWINGS

While the specification concludes with claims particularly pointing out and distinctly claiming the subject matter that is regarded as the present invention, it is believed that the invention will be more fully understood from the following description taken in conjunction with the accompanying drawings.

FIG. 1 is an exploded isometric view of an elastomeric laminate.

FIG. 1A is a cross sectional view of the elastomeric laminate of FIG. 1 through line 1A-1A.

FIG. 1B is an elevation view of an elastomeric laminate which has continuous bonding between a substrate layer and a layer of elastic.

FIG. 1C is an elevation view of an elastomeric laminate which has point bonding between a substrate layer and a layer of elastic.

FIGS. 1D-1F are plan views of a second plurality of elastomeric strands when viewed from the z-direction, looking down at the xy-plane.

FIG. 2 is an exploded isometric view of the elastomeric laminate of FIG. 1 with the added benefit of a second substrate added to the laminate structure.

FIG. 2A is a cross sectional view of the elastomeric laminate of FIG. 2 through line 2A-2A.

FIG. 3 is an exploded isometric view of an elastomeric laminate with the added benefit of a third plurality of elastomeric strands comprising a third plurality of elastomeric strands.

FIG. 3A is a cross sectional view of the elastomeric laminate of FIG. 3 through lines 3A 3A.

DETAILED DESCRIPTION OF THE INVENTION

Figure 3B:
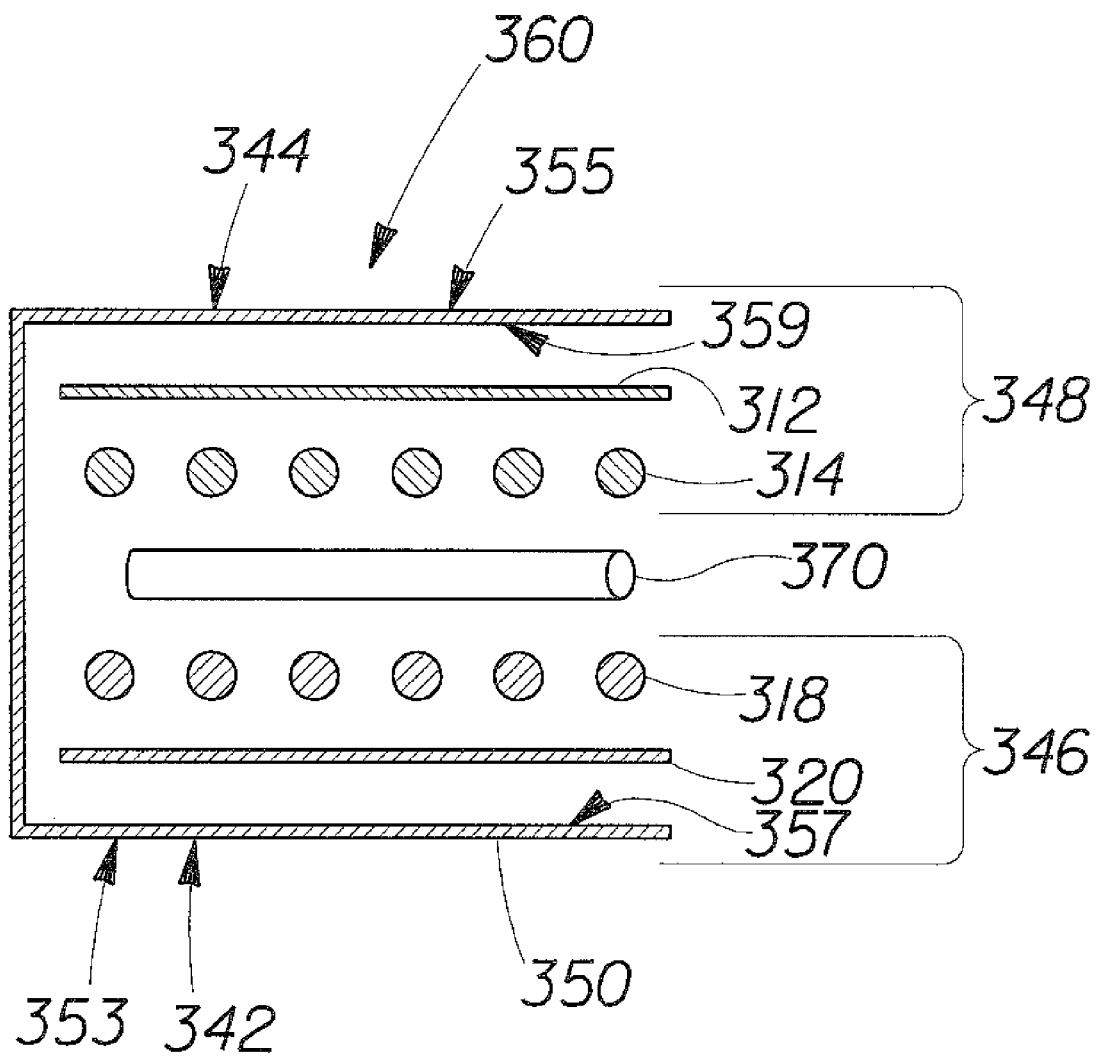
FIG. 3B is a cross sectional view of an alternate embodiment of an elastomeric laminate.

The method, material, and the apparatus of the present invention are designed to provide a more cost effective and/or consumer desirable elastomeric laminate suitable for use in a variety of articles including disposable absorbent articles.

Definitions

The following terminology is used herein consistent with the plain meaning of the terms with further details provided in the present specification.

The terms "activating", "activation" or "mechanical activation" refer to the process of making a substrate, or an elastomeric laminate more extensible than the it was prior to the process.

"Basis weight" refers to the weight of a planar material for a given surface area. Basis weight is typically measured in grams per square meter (gsm). The basis weight of an elastomeric laminate is typically measured in an unstrained configuration.

The terms "corrugations" or "ruggosities" are used to describe hills and valleys that occur in a substrate or in a laminate structure either via the activation or the live stretch processes each described below. Note that neither term mandates that either the hills or valleys created are uniform in nature.

A "disposable absorbent article" refers to an article device that normally absorbs and/or retains fluids. In certain instances, the phrase refers to articles that are placed against or in proximity to the body of the wearer to absorb and contain the excreta and/or exudates discharged from the body, and includes such personal care articles as baby diapers, baby training pants, adult incontinence articles, feminine hygiene articles, baby swim diapers, wound dressing, and the like. A disposable absorbent article may be worn by infants and other incontinent persons about the lower torso.

The term "disposable" is used herein to describe products, which generally are not intended to be laundered or otherwise restored and reused for their original function. They are typically intended to be discarded after about 1 or 2 uses. It is preferred that such disposable articles be recycled, composted or otherwise disposed of in an environmentally compatible manner.

An "elastic," "elastomer" or "elastomeric" refers to polymers or laminates exhibiting elastic properties. They include any material that upon application of a force to its relaxed, initial length can stretch or elongate to an elongated length more than 10% greater than its initial length and will substantially recover back to about its initial length upon release of the applied force.

An "extrusion apparatus" or "extruder" refers herein to any machine capable of extruding a molten stream of material such as a polymeric through one or more extrusion openings.

The term "extrude" or "extruding" refers herein to a process by which a heated elastomer is forced through one or more extrusion openings to form a molten stream of elastic that cools into a solid.

The terms "face to face arrangement" or "face to face orientation" as used herein refer to the joining of a first element to a second element, wherein at least a portion of the first element overlaps at least a portion of the second element or vice versa. Note that the joining of the first element and the second element does not necessarily mean that a face of the first element and a face of the second element are directly bonded or in contact with one another. There may be some intermediate element which resides between the first element and the second element. The first element and the second element in this context may comprise at least one of a substrate, a nonwoven, a plurality of elastomeric strands, or any combination thereof.

The term "force wall" refers herein to situation where a force required for a 10% increase in strain for a given material increases at least about 20%.

The term "joined" herein encompasses configurations whereby a material or component is secured directly or indirectly (by one or more intermediate members) to another material or component. An example of indirect joining is an adhesive. Direct bonding includes heat and or pressure bonding. Joining may include any means known in the art including, for example, adhesives, heat bonds, pressure bonds, ultrasonic bonds, and the like.

"Live stretch" includes stretching elastic and bonding the stretched elastic to a substrate. After bonding, the stretched elastic is released causing it to contract, resulting in a "corrugated" substrate. The corrugated substrate can stretch as the corrugated portion is pulled to about the point that the substrate reaches at least one original flat dimension. However, if the substrate is also elastic, then substrate can stretch beyond the relaxed length of the substrate prior to bonding with the elastic. The elastic is preferably stretched at least 25% and more preferably at least 100% of its relaxed length when it is bonded to the substrate.

The term "longitudinal axis" is used herein to refer to an axis which extends parallel to the longest edge of a laminate or a substrate. If the laminate or substrate has no edge which has a longer length than other edges, then the longitudinal axis extends parallel to an edge if more than one edge or tangent to the edge if only one edge.

The term "transverse axis" is used herein to refer to an axis which extends perpendicular to the longitudinal axis on a laminate or a substrate.

The term "molten stream" refers herein to a linear deposit of a heated liquid material such as a polymeric exiting an extrusion apparatus. The stream may include continuous filaments, discontinuous fibers, or continuous films of a polymeric material. When cooled, the molten stream may form for example, a strand elastic.

The term "machine direction" is used herein to refer to the direction of material flow through a process.

The term "cross direction" is used herein to refer to a direction that is perpendicular to the machine direction.

The term "nonwoven" refers herein to a material made from continuous (long) filaments (fibers) and/or discontinuous (short) filaments (fibers) by processes such as spunbonding, meltblowing, and the like. Nonwovens do not have a woven or knitted filament pattern. Nonwovens are typically described as having a machine direction and a cross direction. The machine direction is the direction in which the nonwoven is manufactured. Nonwovens are typically formed with a machine direction that corresponds to the long or rolled direction of fabrication.

The term "primary direction of extensibility" refers herein to a direction in which an elastomeric laminate provides the lowest resistance to elongation to an applied force.

The term "secondary direction of extensibility" refers herein to a direction in which the elastomeric laminate provides the highest resistance to elongation to an applied force.

The term "substrate(s)" refers herein to a material suitable for use in an elastomeric laminate, particularly for use in a disposable absorbent article. Examples of such materials are films, nonwovens, wovens, fabrics, and other materials known in the art for use in elastomeric laminates in absorbent articles.

Description

Elastomeric laminates are used extensively in absorbent articles. Such laminates have been used in the topsheet, backsheet, waistband, and fastening elements of absorbent articles. In a waistband application, a tension force can be applied to the waistband such that the elastomeric laminate therein is stretched from its non-stretched state to a stretched state. Under initial loading conditions, i.e. fit when the absorbent article is dry, the tension force that can be applied is generally in a primary direction of extensibility of the elastomeric laminate. However, once the absorbent article takes on body exudates and becomes loaded, sagging tension forces which are not predominantly in the primary direction of extensibility are exerted on the elastomeric laminate.

Examples of an elastomeric laminates that can accommodate the sagging tension forces of a loaded absorbent article are provided herein. Each elastomeric laminate discussed herein has a longitudinal axis and a transverse axis. For ease of discussion, coordinate systems have been provided with many of the figures. In each instance, where a coordinate system is referenced, the longitudinal axes are parallel to an x-axis and are parallel to each other as well. Thus, the transverse axes for each coordinate system referenced are also parallel to each other as well.

In one embodiment, as shown in FIGS. 1 and 1A, the elastomeric laminate 100 comprises an extensible intermediate laminate 102 and a second plurality of elastomeric strands 114. The extensible intermediate laminate 102 includes a first substrate 122 which may comprise a first bonding surface 123, an adhesive 120, and a first plurality of elastomeric strands 118. The first plurality of elastomeric strands 118 can be bonded to the first bonding surface 123 of the first substrate 122 via the adhesive 120 or by any means known in the art.

The first plurality of elastomeric strands 118 can be bonded to the first bonding surface 123 of the first substrate 122 along a first orientation (see discussion regarding FIGS. 1D-1F). The first orientation may comprise many different arrangements. As an example, the first plurality of elastomeric strands 118 may be bonded to the first bonding surface 123 of the first substrate 122 where the first orientation 119 is parallel to a longitudinal axis 130 of the elastomeric laminate 100 as shown in FIG. 1 using the coordinate system 199.

Similarly, the second plurality of elastomeric strands 114 may be bonded to the extensible intermediate laminate 102 in a second orientation (see the discussion regarding FIGS. 1D-1F). As shown in FIG. 1, the second plurality of elastomeric strands 114 is joined to the first bonding surface 123 of the first substrate 122 via adhesive 120 or any means known in the art. Alternatively, the second plurality of elastomeric strands may be joined to a face 101 (see FIG. 1A) of the first substrate 122 by any means known in the art.

In order to accommodate the tension forces which act in the primary direction of extensibility, the extensible intermediate laminate 102 can be made extensible via live stretch or mechanical activation. In one embodiment, the extensible intermediate laminate 102 is made extensible in the longitudinal direction 130 via live stretch. The use of live stretch involves the joining of a non-elastic substrate and an elastic while the elastic is in a stretched condition. Once the elastic is bonded to the non-elastic, at least a portion of the strain may be removed from a bonded portion of elastic and non-elastic. Because the elastic is in a stretched condition, when the elastic relaxes, the non-elastic substrate gathers between the locations where it is bonded to the elastic thereby forming corrugations.

Note that depending on the type of bonding, the plurality of elastomeric strands could also corrugate along with the non-elastic substrate. As shown in FIG. 18, if a plurality of elastomeric strands 14 (shown as a sheet in FIGS. 1B and 1C) is continuously bonded to a substrate 10, i.e. bonded substantially throughout their entire length 18, then the corrugations caused by the relaxation of the plurality of elastomeric strands 14 may be present in an entire elastomeric laminate 20. In contrast, as shown in FIG. 1C, if the plurality of elastomeric strands 14 is only bonded at certain points 16 to the substrate 10, then the substrate 10 will generally corrugate with the bonded points 16 corresponding to corrugation valleys 24 and in between the bonded points the corrugation hills 22.

The corrugation hills 22 and valleys 24 determine the corrugation direction depending on which way they extend. If the corrugation hills and corrugation valleys extend in a transverse direction 140 (see coordinate system 198), the corrugation direction is the transverse direction 140. The substrate 10 and/or elastic laminate is generally extensible perpendicular to the corrugation direction. For the elastic laminates 20 and 30, the corrugation direction 75 may be in the transverse direction 140. Therefore, the overall elastomeric laminate may be extensible in the longitudinal direction 130.

In contrast to live stretch, mechanical activation physically manipulates the elastic laminate such that it becomes elastomeric. The mechanical activation process utilizes "zero strain" stretch laminate webs which comprise at least two plies of material secured to one another along at least a portion of their coextensive surfaces while in a substantially untensioned ("zero strain") condition. One of the plies employed in the "zero strain" stretch laminate is comprised of a material, which is stretchable and elastomeric, i.e., it will return substantially to its untensioned dimensions after an applied tensile force has been released. The second ply secured to the elastomeric ply is elongatable but not necessarily elastomeric. Upon stretching, the second ply will permanently elongate at least to a certain degree, so that upon release of the applied tensile forces, it will not fully return to its original undistorted configuration. The stretching is induced by mechanical activation which may include, for example meshing the laminate between corrugated mating rolls.

Despite the fact that the second orientation is shown to comprise a curvilinear component (see FIG. 1), the second orientation can vary to the same degree as the first orientation; however, for the sake of simplicity, reference shall only be made to the second orientation when discussing FIGS. 1D-1F. In addition, coordinate system 197 shall be referenced for FIGS. 1D-1F.

In order to accommodate tension forces which generally do not act parallel to the primary direction of extensibility of the elastomeric laminate, e.g. the sagging tension forces which are exerted on an elastomeric laminate from an absorbent article, the second orientation 115 preferably comprises a curvilinear component 177 as shown in FIG. 1D. The curvilinear component 177 may be either concave or convex with respect to the longitudinal axis 130 or the transverse axis 140, or an elastomeric strand or the second plurality of elastomeric strands may comprise a plurality of curvilinear components thereby having both concave and convex curvilinear components. The curvilinear component 177 may have radii of curvature greater than about 1 mm, preferably greater than about 10 mm, more preferably greater than about 50 mm. The radii curvature may optionally be variable over the length or "path" of the curvilinear component 177.

The addition of the curvilinear component 177 can increase the contracting force exerted by the elastomeric laminate in the primary direction of extensibility and also increase the modulus of elasticity in the secondary direction of extensibility. For example, the center portion 176 of laminate 103 comprises the second plurality elastomeric strands 114 which include a curvilinear component 177. Within the center portion 176, the curvilinear component 177 provides physically more elastomeric material in the center portion 176 than there would be if the strands were merely straight lines extending through the center portion 176. Because the curvilinear component 177 physically provides more elastomeric material which increases the contracting force in the primary direction of extensibility and also increases the modulus of elasticity of the elastomeric laminate.

As another example, as shown in FIG. 1E, the second plurality of elastomeric strands 114 can be bonded to the extensible intermediate laminate where the second orientation 115 is at a predetermined angle 116 from the longitudinal axis 130 of the elastomeric laminate 104. The pre-determined angle 116 can range from zero to 360 degrees from the longitudinal axis 130. Therefore, the second orientation 115 could in theory be parallel to the first orientation 119; however, the second orientation 115 is preferably different from and therefore deviates from the first orientation 119. In addition, in order to accommodate the curvature of a wearer's body, the second orientation 115 is preferably non-orthogonal to the first orientation 119. The second orientation 115 of the second plurality of elastomeric strands 114 may also comprise combinations of the arrangements described above as shown in FIG. 1F.

When an elastomeric laminate is utilized in an article, exposure of a wearer's skin to a plurality of elastomeric strands, as described above, could lead to skin irritation because of the expansion and contraction of the elastomeric strands. A second substrate is preferably included with the previously discussed elastomeric laminate 100 of FIG. 1 as shown in FIGS. 2 and 2A in order to reduce the likelihood of this irritation. With regard to FIG. 2, coordinate system 299 shall be referenced.

A second substrate 210 having a second bonding surface 211 is included with an elastomeric laminate 200. The elastomeric laminate 200 further comprises the extensible intermediate laminate 102 and the second plurality of elastomeric strands 114 as described previously. The second plurality of elastomeric strands 114 can be bonded to the second bonding surface 211 of the second substrate 210 via the adhesive 212 or by any means known in the art. The second substrate 210 can be joined to the extensible intermediate laminate 102 in a face to face arrangement.

Preferably, the elastomeric laminate 200 is extensible in a direction parallel to the longitudinal axis 230 even with the addition of the second substrate 210. The second substrate 210 may be added to the extensible intermediate laminate 102 and the second plurality of elastomeric strands 114 while the extensible intermediate laminate 102 and the second plurality of elastomeric strands 114 is at least partially extended such that the elastomeric laminate 200 may be extensible in a direction that is parallel to the longitudinal axis 230. Optionally, the second substrate 210 may be added to the extensible intermediate laminate 102 while the extensible intermediate laminate 102 is in a relaxed state. The resulting elastomeric laminate 200 may be mechanically activated such that the elastomeric laminate 200 is extensible in a direction parallel to the longitudinal axis 230. Optionally, after the second substrate 210 is added to the extensible intermediate laminate 102, the extensible intermediate laminate 102 may be mechanically activated such that the elastomeric laminate 200 is extensible in a direction that is not parallel to the longitudinal axis 230, e.g. the elastomeric laminate 200 can be made extensible in a direction parallel to the transverse axis 240.

In another embodiment, an elastomeric laminate 300 may comprise a first extensible intermediate laminate 302, a second extensible intermediate laminate 304, and a third plurality of elastomeric strands 370 as shown in FIGS. 3 and 3A. With regard to FIG. 3 coordinate system 399 shall be referenced.

The embodiment of FIGS. 3-3B have the added benefit of providing more contracting force while accommodating the higher sagging tension forces present in a loaded absorbent article. The first extensible intermediate laminate 302 comprises a first substrate 322 which has a first bonding surface 323. A first plurality of elastomeric strands 318 extending along a first orientation 319 can be bonded to the first bonding surface 323 of the first substrate 322 via an adhesive 320 or by any means known in the art.

The first orientation 319 can vary in accordance with the discussion of the second orientation in FIGS. 1D-1F. As an example, as shown in FIG. 3, the first orientation 319 can be parallel to a longitudinal axis 330. The first extensible intermediate laminate 302 can be made extensible in a direction parallel to the longitudinal axis 330 via the live stretch process or the mechanical activation process as discussed previously.

The second extensible intermediate laminate 304 may comprise a second substrate 310 having a second bonding surface 311. A second plurality of elastomeric strands 314 extending along a second orientation 315 may be bonded to the second bonding surface 311 of the second substrate 310 via an adhesive 312 or any means known in the art. The second orientation 315 can vary in accordance with the discussion of the second orientation in FIGS. 1D-1F except that the first orientation 319 is not necessarily different from the second orientation 315. In addition, the second extensible intermediate laminate 304 can be made extensible via the live stretch process or the mechanical activation process as discussed previously.

Preferably, in order to provide more contracting force, the first orientation 319 and the second orientation 315 are linear in nature and are parallel to the longitudinal axis 330. In one embodiment, the first extensible intermediate laminate 302 and the second extensible intermediate laminate 304 are extensible in a direction parallel to the longitudinal axis 330 and can be made extensible via the live stretch process or the mechanical activation process as discussed previously.

The third plurality of elastomeric strands 370 extend along a third orientation 375 and may be bonded to the first extensible intermediate laminate 302 and the second extensible intermediate laminate 304 by any known means or method known in the art. The third orientation 375 can vary in accordance with the discussion of the second orientation in FIGS. 1D-1F. The third orientation 375 should be different from the first orientation 319 and the second orientation 315 such that the third orientation can provide at least some accommodation to the sagging tension forces which are exerted on an elastomeric laminate from a loaded absorbent article. The third orientation 375 may comprise a curvilinear component (see 177 in FIG. 1D). Additionally, the third orientation 375 may correspond to an arrangement that is at an angle (see 116 in FIG. 1E) from the primary direction of extensibility, which is parallel to the longitudinal axis 330. In order to accommodate the sagging tension forces exerted by a loaded absorbent article, the angle is preferably greater than about 20 degrees and less than about 160 degrees from the longitudinal axis 130.

The first extensible intermediate laminate 302 and the second extensible intermediate laminate 304 may be joined in a face to face orientation with the third plurality of elastomeric strands 370 disposed therebetween. However, the third plurality of elastomeric strands 370 can be joined to a face 301 of the first extensible intermediate laminate 302 or a face 303 of the second extensible intermediate laminate 304 and is not necessarily limited to being joined between the first extensible intermediate laminate 302 and the second extensible intermediate laminate 304.

In another embodiment, an elastomeric laminate 360, as shown in FIG. 3B, can be created using a single substrate 350. The single substrate 350 may comprise a first portion 342 and a second portion 344. The first portion 342 can act as the first substrate and the second portion 344 can act as the second substrate. A first plurality of elastomeric strands 318 may be bonded to the first portion 342 via an adhesive 320 that is applied to the first portion 342 thereby forming a first extensible intermediate laminate 346. A second plurality of elastomeric strands 314 may be bonded to the second portion 344 via an adhesive 312 that is applied to the second portion 344 thereby forming a second extensible intermediate laminate 348. A third plurality of elastomeric strands 370 may be bonded to a face 353, 357 of the first intermediate laminate 346 or a face 355, 359 of the second intermediate laminate 348. The second portion 344 can be folded on top of the first portion 342 such that the first portion 342 and the second portion 344 are in a face-to-face orientation or vice versa.

Instead of folding the second portion 344 on top of the first portion 342 or vice versa, the single substrate 350 can be slit such that the first intermediate laminate 346 and the second intermediate laminate 348 form two distinct webs which are joined in a face to face arrangement. Alternatively, the single substrate 350 can be slit such that the first portion 342 and the second portion 344 form two distinct webs which are processed and subsequently joined in a face to face arrangement.

The first plurality of elastomeric strands 318 and the second plurality of elastomeric strands 314 can be pre-strained prior to their bonding to the first portion 342 and second portion 344, respectively, such that the first and second portions 342, 344 are extensible. Alternatively, the first plurality of elastomeric strands 318 and the second plurality of elastomeric strands 314 can be bonded to the first portion 342 and second portion 344 in a relaxed state, and subsequently, the elastomeric laminate 360 can be mechanically activated such that it is extensible.

Suitable apparatuses for extruding the first plurality of elastomeric strands, the second plurality of elastomeric strands, and optionally the third plurality of elastomeric strands in the first, second, and third orientations, respectively, are discussed below. Apparatuses for applying elastomeric strands in a longitudinal direction are described in U.S. application Ser. No. 10/452,438 entitled "Method and Apparatus for Producing Elastomeric Nonwoven Laminates" filed on Jun. 2, 2003 and in U.S. application Ser. No. 10/836,944 entitled "Apparatus for Producing Elastomeric Nonwoven Laminates" filed on Apr. 30, 2004. Apparatuses for applying elastomeric strands in a transverse direction, an angle from the longitudinal direction, or in a curvilinear fashion are described in U.S. application Ser. No. 10/779,338 entitled "Method of Placing Material Transversely on a Moving Web" filed on Feb. 13, 2004. Apparatuses for applying elastomeric strands in the longitudinal direction, an angle from the longitudinal direction, or in a curvilinear fashion are described in U.S. application Ser. No. 10/834,539 entitled "Extrusion Applicator Having Linear Motion Operability" filed on Apr. 29, 2004, and in U.S. application Ser. No. 10/834,503 entitled "Extrusion Applicator Having Rotational Operability" filed on Apr. 29, 2004.

Suitable apparatuses and methods for printing elastomeric strands in any of the above mentioned orientations and combinations thereof are described in U.S. Application No. 60/557,272 entitled "Letterpress Application of Elastomeric Compositions" filed on Mar. 29, 2004, in U.S. Application No. 60/557,245 entitled "Method of Gravure Printing Elastomeric Compositions" filed on Mar. 29, 2004, in U.S. application Ser. No. 10/811,671 entitled "Variable Stretch Composites and Methods of Making the Composite" filed on Mar. 29, 2004, and in U.S. application Ser. No. 10/811,527 entitled "Variable Stretch Composites and Methods of Making the Composite" filed on Mar. 29, 2004.

As mentioned previously, an elastomeric laminate comprises a substrate layer and a layer of elastic or a plurality of elastomeric strands. The first substrate and second substrate for any of the elastomeric laminates disclosed herein may comprise any material known in the art for the construction of elastomeric laminates. Preferably, both the first and second substrates comprise nonwovens. If the first or second substrate comprise nonwovens, then the nonwovens may comprise fibers made of polypropylene, polyethylene, polyester, nylon, cellulose, polyamide, or combinations of such materials. Fibers of one material or fibers of different materials or material combinations may be used in the first and/or second nonwoven. Exemplary nonwoven materials include spunbond, spunbond meltblown spunbond (SMS), spunbond meltblown meltblown spunbond (SMMS), carded and the like. Particularly acceptable nonwovens include high elongation carded (HEC) nonwovens and deep activation polypropylene (DAPP) nonwovens. Any process known in the art may be used to make the nonwovens.

The nonwoven may comprise fibers that are bonded internally, including fibers that are needle punched, hydro entangled, spun bonded, thermally bonded, bonded by various types of chemical bonding such as latex bonding, powder bonding, and the like. Preferably, the basis weight of the first nonwoven and/or second nonwoven is in the range of about 10 gsm to about 40 gsm. The basis weight of the first nonwoven and the second nonwoven may range from about 10 gsm to about 40 gsm.

The first substrate or second substrate may comprise more than one layer of nonwoven material. For example the first substrate may include a nonwoven adhesively bonded to another nonwoven that is then bonded to the plurality of elastic strands. Similarly, the second substrate may include a nonwoven bonded to another nonwoven the combination of which is bonded to the intermediate laminate and subsequently activated.

The first substrate, second substrate and a plurality of elastomeric strands may be joined by any joining means known in the art. Some examples of suitable joining means and/or methods for joining include, but are not limited to, adhesives, cohesives, thermal bonding, pressure bonding, mechanical bonds, ultrasonic bonding, and/or any combination of any known methods of joining such materials.

A plurality of elastomeric strands may extend in a generally parallel spaced relationship between the first substrate and the second substrate. However, the elastomeric strands may be arranged in any configuration desired. For instance, the strands may be arranged to provide a specific force profile in the elastomeric laminate by varying the thickness of the individual strands or the spacing between them. Moreover, the strands may be continuous extending substantially across a face of a substrate or may comprise discrete portions which extend substantially across the face of the substrate.

The plurality of elastic strands is preferably made of a resiliently elastic thermoplastic material. The elastic strands may be made from liquid elastic that is extruded through a die to achieve the desired strand elastic diameter and/or shape. The shape of the extruded elastic strands is not limited. For example, typical elastic strands have a circular cross sectional shape, but sometimes the plurality of elastic strands may have different shapes, such as a trilobal shape, or a flat (i.e., "ribbon" like) shape. Suitable elastomeric strand shapes (not all shown) include rectangles, circles, ellipses, diamonds, triangles, parallelograms, trapezoids, wedges or other sections of circles or ellipses, other polygons, or other irregular enclosed shapes. Furthermore, the thickness or diameter of the elastic strands may vary in order to accommodate a particular application. Typically, the thickness of elastomeric strands may be in the range of about 0.02 mm to about 1 mm and the basis weight is in the range of about 20 $g/m^2$ to about 300 $g/m^2$.

For the printing of elastomeric strands, the individual elastomeric strands may be configured as lines or strands generally having widths less than about 2 mm and typically less than about 1 mm. Linear elastomeric strands may be configured as bands generally have widths between about 2 mm and about 20 mm and aspect ratios ranging from about 2:1 to about 100:1. Typically, the thickness of an elastomeric strand may be in the range of about 0.02 mm to about 5 mm and the basis weight is in the range of about 20 $g/m^2$ to about 300 $g/m^2$.

Figure 4:
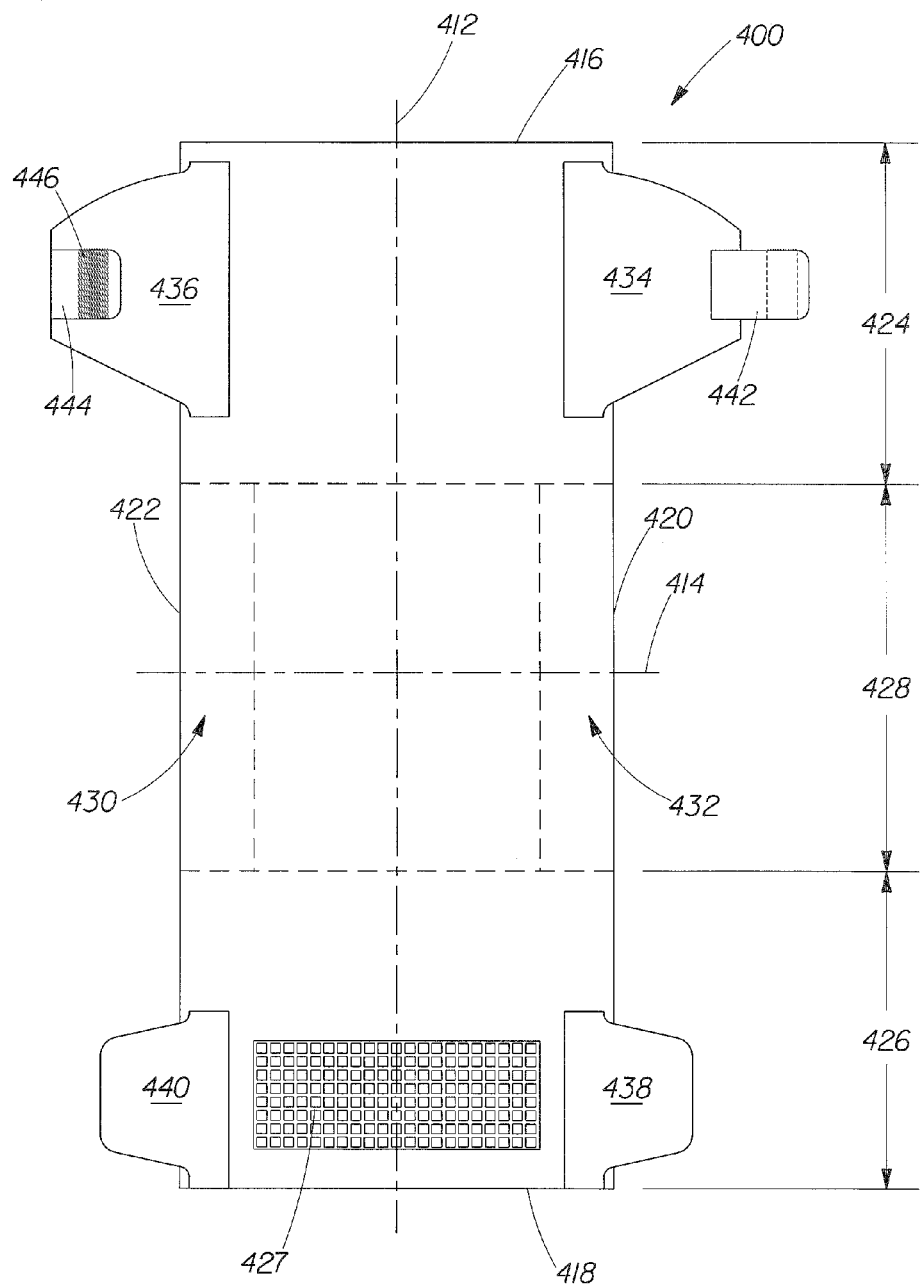
FIG. 4 is a plan view of a diaper in accordance with the invention.
Figure 4A:
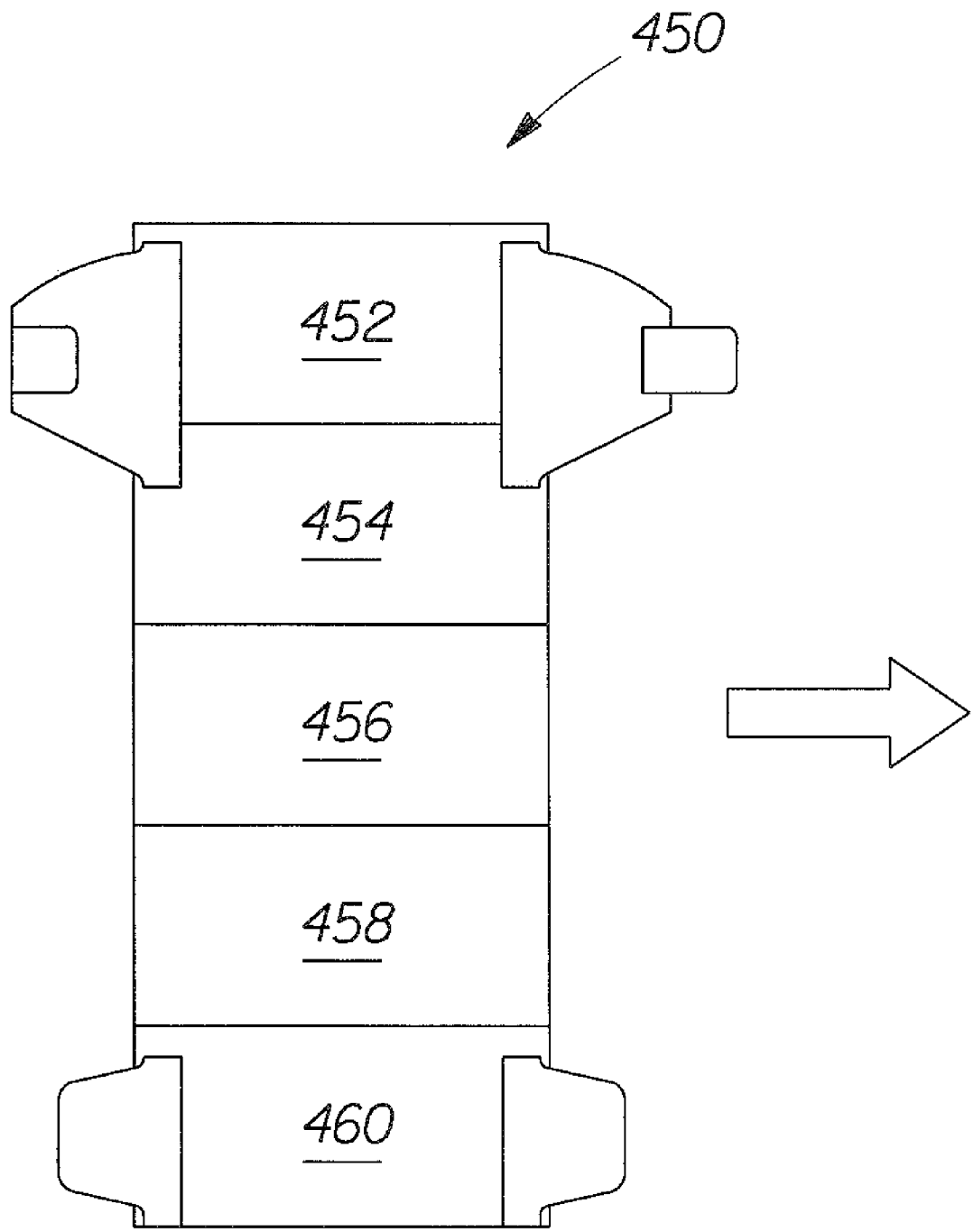
FIG. 4A illustrates various regions of a diaper where elastomeric laminates may be used.
Figure 5:
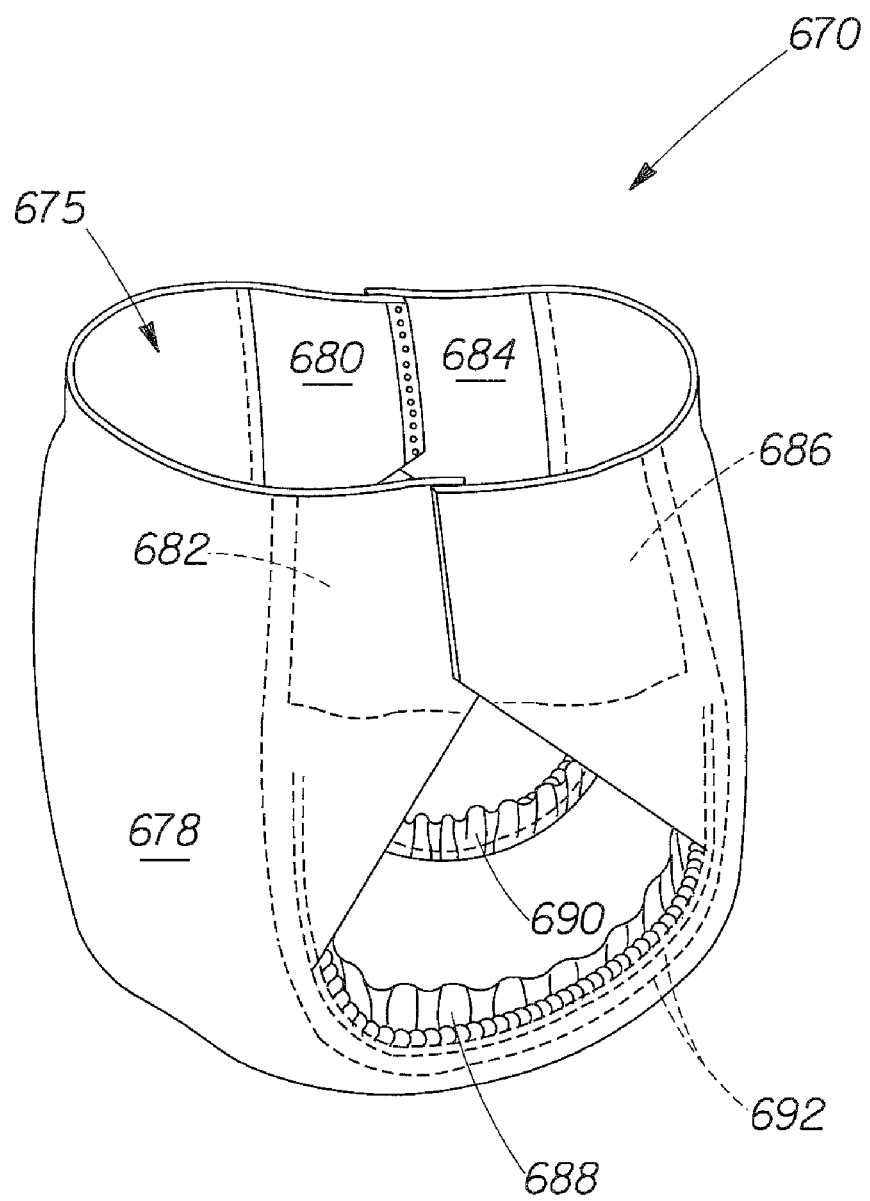
FIG. 5 is a perspective view of a pull-on diaper in accordance with the invention.
Figure 6:
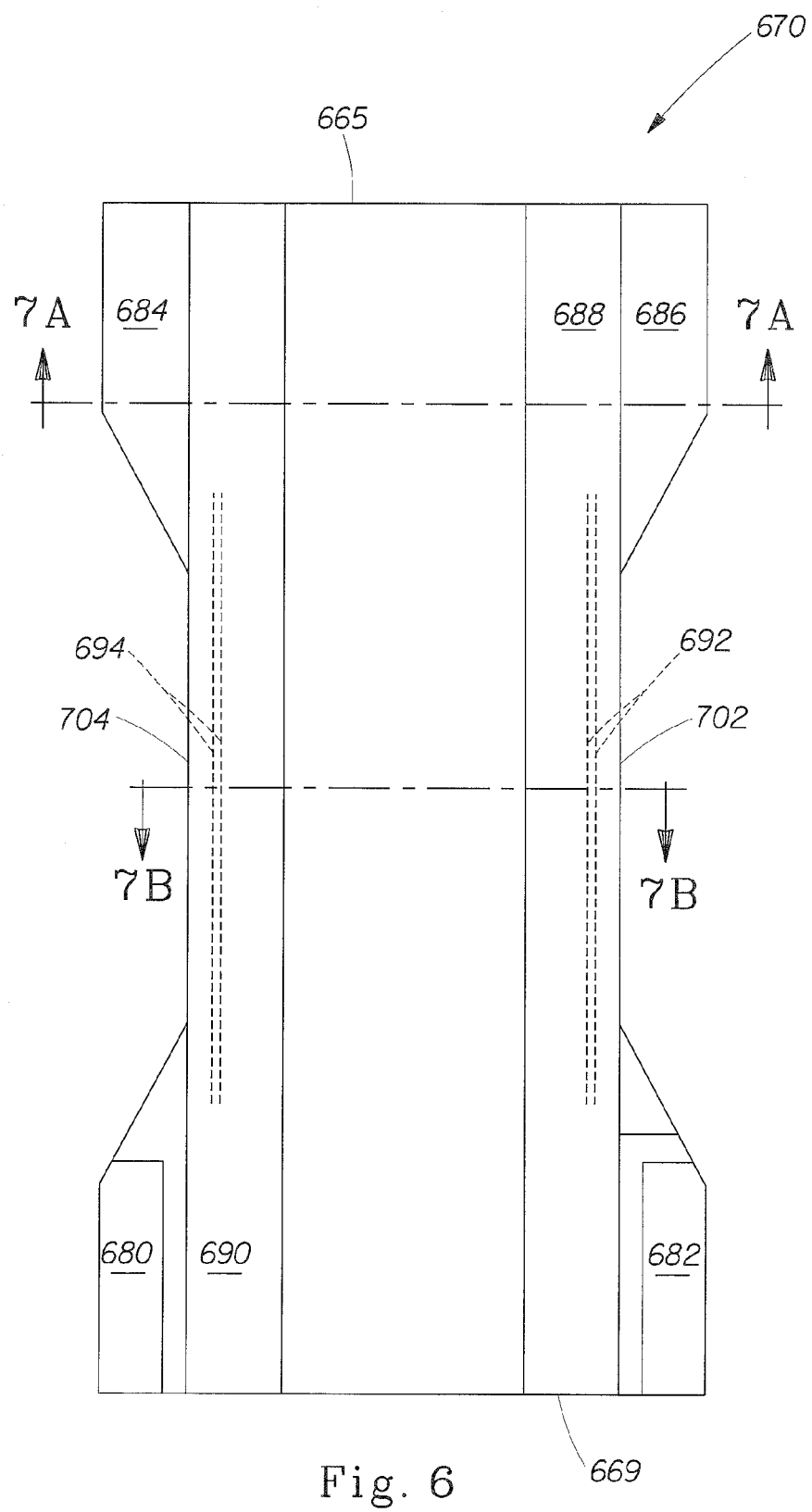
FIG. 6 is a plan view of the pull-on diaper of FIG. 5 shown in a flattened state.

Examples of the potential uses of the elastomeric laminates described herein in an absorbent article are provided below. Referring collectively to FIGS. 4-4A, an absorbent article in the form of an open-style or taped diaper 400 is depicted. It should be understood that while FIGS. 4-6 depict a diaper, the present invention also contemplates other wearable absorbent articles that encircle or enclose at least a portion of a wearer's anatomy or which are otherwise secured to a wearer. The diaper 400 has a longitudinal centerline 412 and a lateral centerline 414 as a frame of reference for this discussion. The diaper 400 may have a pair of opposed longitudinal edges 416 and 418, a pair of opposed lateral edges 420 and 422, a rear waist region 424, a front waist region 426, a crotch region 428 disposed intermediate the front and rear waist regions 426 and 424, respectively, and a pair of leg regions 430 and 432.

The diaper 400 also may comprise one or more ear or side panels 434, 436, 438 and 440 disposed laterally outboard of the front waist region 426 and/or rear waist region 424. In closable diaper 400 embodiments, at least one fastener element 442 is disposed on one or more of side panels 434 and 436 and is adapted to be secured to at least a portion of the longitudinally opposing front side panels 438 and 440, or a portion of the outer surface of the front waist region 426 or a component thereof. An accompanying fastener element 444 is shown in a folded back configuration to expose the mechanical fasteners 446, which shown as hooks for a hook-and-loop fastening system commercially available from 3M or Velcro Industries. The fastener element 444 may be capable of engaging loop material embodied in a landing zone 427 located on the outer surface of the diaper 400.

Any one or more of regions 424, 426, 428, 430, 432, 434, 436, 438, 440, 442 or 444 may comprise an elastomeric laminate as described herein. In this way, the diaper 400 may preferably be configured to adapt to the specific wearer's anatomy upon application and to maintain coordination with the wearer's anatomy during wear (i.e., the fit should remain the same with minimal sagging, achieving sustained fit).

An exemplary diaper chassis comprising arrays of elastomeric laminates is diaper chassis 450 of the diaper 400 shown in FIG. 4A. The diaper chassis 450 may include a liquid impermeable backsheet and an outer cover made of a nonwoven material. Other chassis components may be included but are not depicted for purposes of clearly showing the multi-variant arrays of the present invention. The backsheet may comprise the elastomeric laminates described above such that the stretch properties of regions 452, 454, 456, 458, and 460 are different from one another. Specifically, the elastomeric laminates may be oriented in different directions in these regions in order to best accommodate the curvature of the wearer's body as well as the sagging tension forces. By way of example, region 452 may comprise an elastomeric laminate which comprises a second plurality of strands which comprise a curvilinear component while region 454 may comprise an elastomeric laminate which comprises a second plurality of elastomeric strands wherein the second orientation comprises a pre-determined angle from a longitudinal axis of the elastomeric laminate. In certain cases for purposes of enhancing fit on a wearer, the various elastomeric laminate properties are symmetrical in that regions 452 and 460 have similar properties, regions 454 and 458 also have similar properties while region 456 has a third type of property. It should be understood, however, that this is not necessary and that individual regions 452, 454, 456, 458 and 460 may vary individually and widely in terms of properties, size, and shape, without deviating from the scope of the invention.

Reference is now made to FIGS. 5, 6, and 7A-7B which show a pant 670. The term "pant", as used herein, refers to disposable garments having a waist opening and leg openings designed for infant or adult wearers. A pant may be preformed by any suitable technique including, but not limited to, joining together portions of the article using refastenable and/or non-refastenable bonds (e.g., seam, weld, adhesive, cohesive bond, fastener, etc.). A pant may be preformed anywhere along the circumference of the article (e.g., side fastened, front waist fastened). While the term "pant" is used herein, pants are also commonly referred to as "closed diapers", "prefastened diapers", "pull-on diapers", "training pants" and "diaper-pants". Suitable pants are disclosed in U.S. Pat. Nos. 5,246,433, 5,569,234, 6,120,487, 6,120,489, 4,940,464, 5,092,861, U.S. patent application Ser. No. 10/171,249, entitled "Highly Flexible And Low Deformation. Fastening Device", filed on Jun. 13, 2002; U.S. Pat. Nos. 5,897,545, 5,957,908.

For pant diaper 670, as shown in FIG. 5, the elastomeric laminates of the present invention may be included anywhere on the pant diaper 670. On the outer surface of the pant diaper 670, an outer cover 678 typically comprising a nonwoven can be disposed. The outer cover 678 can be joined to a backsheet (see 674 in FIGS. 7A-7B) so as to form a portion of a pair of leg openings and a waist opening for the wearer. Also, two pair of side panels 680, 682, and 684, 686 are attached to the outer cover 678.

Figure 7A:
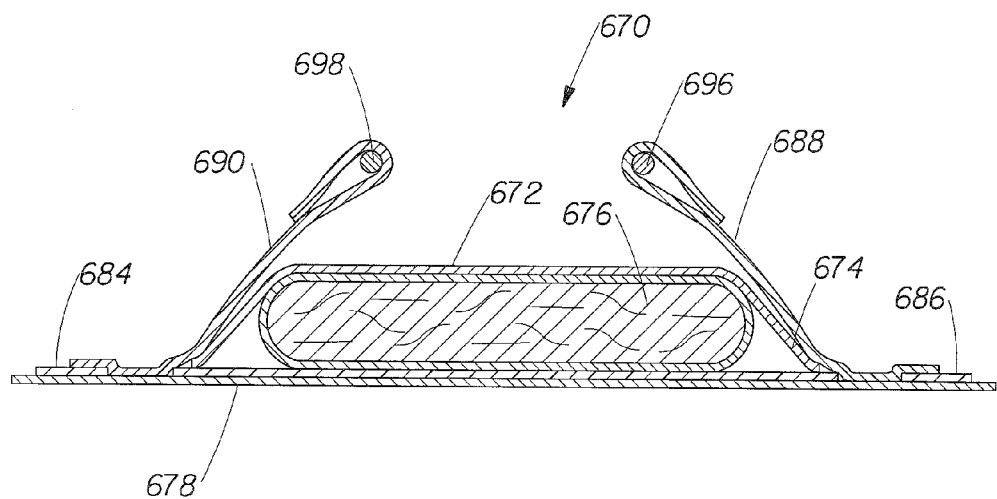
FIGS. 7A and 7B are cross-sectional views of the pull-on diaper shown in FIG. 5-6.
Figure 7B:
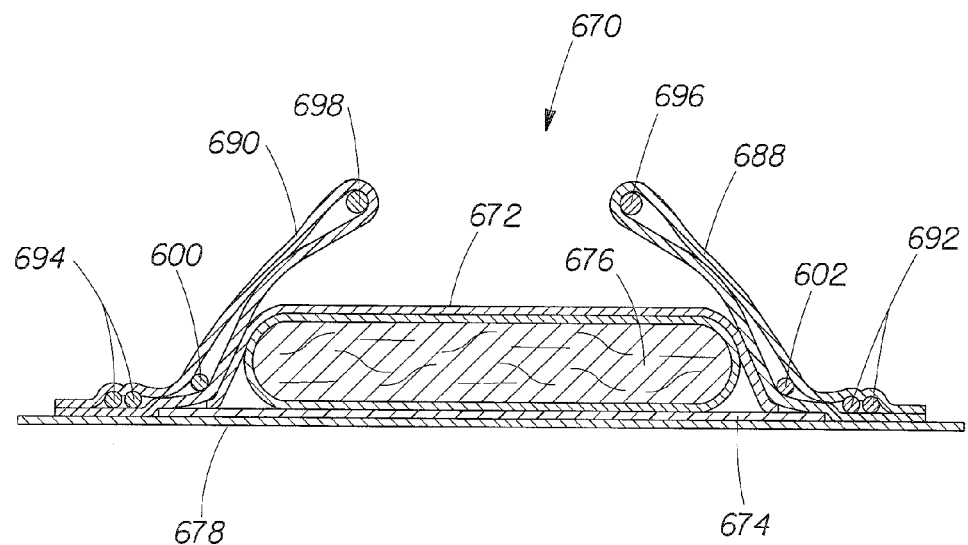

The two of the side panels 680 and 684 extend outward from a longitudinal edge 704 as shown in FIG. 6. The other two side panels 686 and 682 extend outward from a longitudinal edge 702. The elastomeric laminates disclosed herein may be incorporated into the two pair of side panels 680, 682, and 684, 686 in order to accommodate the tension forces, the sagging tension forces, and the contours of a wearer's body. The elastomeric laminates of the present invention may also be incorporated into pant 670 in a waist feature (not shown) that is disposed adjacent end edges 665 and 669 or barrier leg cuffs 688 and 690. In addition, the pant diaper 670 may include an absorbent assembly including liquid permeable topsheet 672, a liquid impermeable backsheet 674, and an absorbent core 676 disposed between the topsheet 672 and the backsheet 674 as shown in FIGS. 7A-7B.

Belt structures (not shown) may also comprise the elastomeric laminates of the present invention. One such alternative structure comprises the ear and/or side panel and at least a portion of the waist functionality. In another alternative belt structure, a belt completely encircling a wearer's waist (i.e. a 360 degree belt) may be formed, referring to FIG. 6 for example, by incorporating one or more elastomeric laminates of the present invention adjacent the front and rear waist edges 665, 669 so as to form a band of tension about the wearer's waist.

Figure 8:
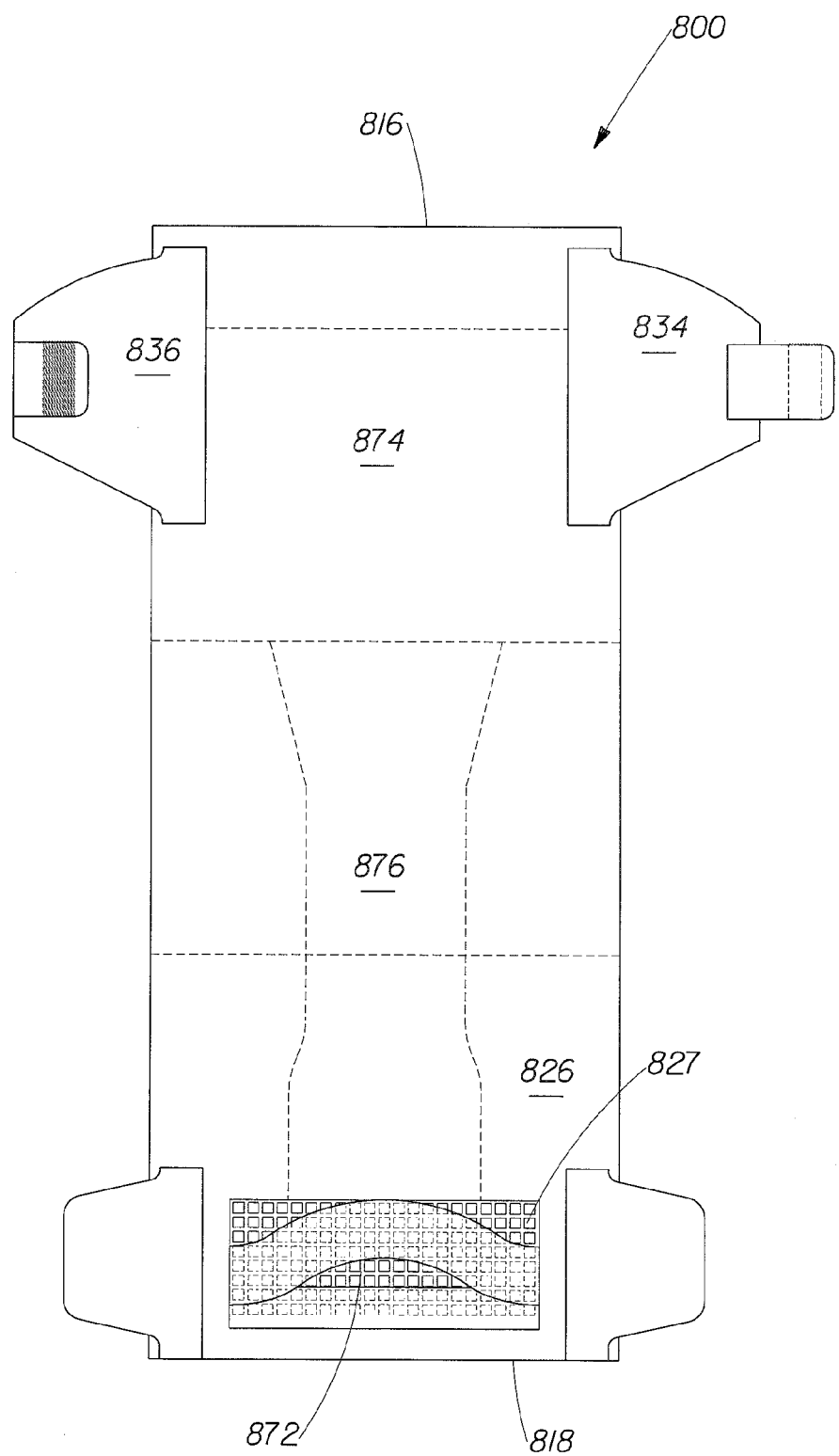
FIG. 8 is a plan view of a diaper in accordance with the invention in which elastomeric laminates are disposed in the diaper ears and the front waist portion.

Referring to FIG. 8, another embodiment of diaper 800 is depicted in which the front waist region 826 may comprise at least one elastomeric laminate of the present invention. The function of elastomeric laminate is to dynamically accommodate the contraction and expansion cycles of the wearer's abdomen as the wearer moves and/or changes position, preventing front waist sagging. The elastomeric laminate is preferably substantially aligned with the front waist end 818 of the diaper 800. In closable versions of diaper 800 including a fastening landing zone 827 disposed in or near the front waist end 818, the landing zone 827 may be shaped in a configuration presenting a concavity to the front waist end 818 of the diaper 800. In these embodiments, elastomeric laminate may at extend into the landing zone 827 concavity 872 as shown in FIG. 8.

Figure 9:
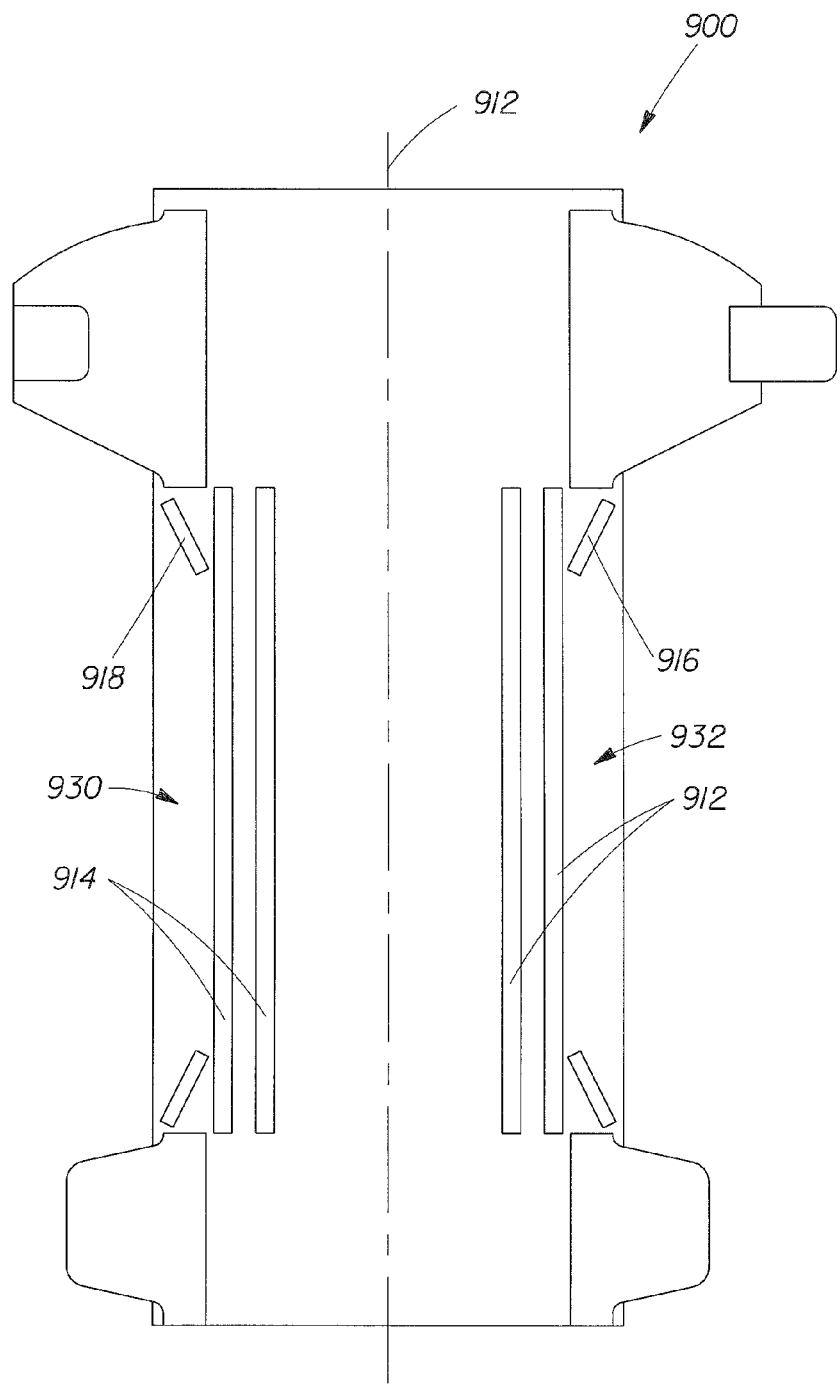
FIG. 9 is a plan view of a diaper in which elastomeric laminates are disposed along the lateral portions of a diaper in order to provide the desired elastic properties in the leg openings.

Referring to FIG. 9, diaper 900 is shown in which leg regions 930 and 932 may comprise elastomeric laminates 912 and 914. Portions of the leg regions 930 and 932 may comprise one or more additional elastomeric laminates 916 and 918 such that a plurality of elastomeric strands are oriented at an angle to the longitudinal centerline 912 of diaper 900. Typically, either the first or second plurality of elastomeric strands may be at an angle of about 45 degrees to about 90 degrees from the longitudinal centerline 912.

All of the embodiments of the elastomeric laminates in FIGS. 1-3B may be incorporated into diaper components which may take any one or more of the materials, designs, and methods of assembly described hereinafter without departing from the scope of the present invention. While any of the article components may be assembled in a variety of well known configurations, exemplary diaper configurations are described generally in U.S. Pat. Nos. 3,860,003; 5,151,092; and 5,221,274; and 5,554,145; 5,569,234; 5,580,411; and 6,004,306.

The absorbent articles described herein can utilize a variety of materials in their manufacture. Some examples of the materials which can be used in the manufacture of absorbent articles are provided below; however, the list of materials provided is by no means exhaustive. For example, breathable materials, which are used extensively in absorbent articles may include materials such as woven webs, nonwoven webs, composite materials such as film-coated nonwoven webs, microporous films such as manufactured by Mitsui Toatsu Co., of Japan under the designation ESPOIR NO and by Exxon Chemical Co., of Bay City, Tex., under the designation EXXAIRE, and monolithic films such as manufactured by Clopay Corporation, Cincinnati, Ohio under the name HYTREL blend P18-3097. Some breathable composite materials are described in greater detail in U.S. Pat. Nos. 6,187,696; 5,938,648; 5,865,823; and 5,571,096.

The article may also include a structural elastic-like film web is an extensible material that exhibits an elastic-like behavior in the direction of elongation without the use of added elastic materials and is described in more detail in U.S. Pat. No. 5,518,801. In alternate embodiments, the backsheets may comprise elastomeric films, foams, strands, or combinations of these or other suitable materials with nonwovens or synthetic films.

Exemplary absorbent structures for use as the absorbent core are described in U.S. Pat. Nos. 4,610,678; 4,673,402; 4,834,735; 4,888,231; 5,137,537; 5,147,345; 5,342,338; 5,260,345; 5,387,207; and 5,625,222.

Suitable absorbent and nonabsorbent sublayers are described in European Patent Application No. EP 0 847 738 A1 and U.S. Pat. No. 5,941,864. Further, the sublayer, or any portion thereof, may include or be coated with a lotion or other known substances to add, enhance or change the performance or other characteristics of the element.

Some exemplary surface fastening, systems are disclosed in U.S. Pat. Nos. 3,848,594; B1 4,662,875; 4,846,815; 4,894,060; 4,946,527; the herein before referenced U.S. Pat. Nos. 5,151,092; and 5,221,274. An exemplary interlocking fastening system is disclosed in co-pending U.S. application Ser. No. 09/143,184 entitled "Absorbent Article Fastening Device" in the names of Kline et al. filed on Aug. 8, 1998. The fastening system may also: provide a means for holding the article in a disposal configuration as disclosed in U.S. Pat. No. 4,963,140; include primary and secondary fastening systems, as disclosed in U.S. Pat. No. 4,699,622; means to reduce shifting of overlapped portions or to improve fit as disclosed in U.S. Pat. No. 5,242,436. means to resist gapping at a wearer's belly as disclosed in U.S. Pat. Nos. 5,499,978 in 5,507,736 and in 5,591,152.

Suitable training pants and pull-on diapers are disclosed in U.S. Pat. Nos. 5,246,433; 5,569,234; 6,120,487; 6,120,489; 4,940,464; and 5,092,861.

Examples of diapers with elasticized side panels are disclosed in U.S. Pat. Nos. 4,857,067; 4,381,781; 4,938,753; the herein before referenced U.S. Pat. Nos. 5,151,092; 5,221, 274; 5,669,897; and 6,004,306.

U.S. Pat. No. 3,860,003 describes a disposable diaper which provides a contractible leg opening having a side flap and one or more elastic members to provide an elasticized leg cuff (a gasketting cuff). U.S. Pat. Nos. 4,808,178 and 4,909,803 describe disposable diapers having "stand-up" elasticized flaps (barrier cuffs) which improve the containment of the leg regions. U.S. Pat. Nos. 4,695,278 and 4,795,454 describe disposable diapers having dual cuffs, including gasketting cuffs and barrier cuffs.

Embodiments of the present invention may also include pockets for receiving and containing waste, spacers which provide voids for waste, barriers for limiting the movement of waste in the article, compartments or voids which accept and contain waste materials or any combinations thereof. Examples of pockets and spacers for use in absorbent products are described in U.S. Pat. Nos. 5,514,121; 5,171,236; 5,397,318; 5,540,671; 6,168,584; 5,306,266; and 5,997,520. Examples of compartments or voids are disclosed in U.S. Pat. Nos. 4,968,312; 4,990,147; 5,062,840; and 5,269,755. Examples of suitable transverse barriers are described in U.S. Pat. Nos. 5,554,142; 6,010,490; and 5,653,703. Examples of other structures especially suitable for management of low viscosity feces are disclosed in U.S. Pat. Nos. 5,941,864; 5,977,430 and 6,013,063.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A process for producing an elastomeric nonwoven laminate, the process comprising the steps of:
   advancing a first nonwoven in a machine direction, the first nonwoven having a longitudinal axis parallel with the machine direction, and the first nonwoven having a first surface and second surface, wherein the first surface is disposed opposite the second surface;
   stretching a first plurality of elastomeric strands in the machine direction;
   bonding the stretched first plurality of elastomeric strands to the first surface of the first nonwoven along a first orientation, wherein the first orientation is parallel with the machine direction;
   corrugating the first nonwoven by allowing the stretched second plurality of elastomeric strands to relax in the machine direction;
   advancing a second nonwoven in the machine direction, the second nonwoven having a longitudinal axis parallel with the machine direction, the second nonwoven having a first surface and second surface, wherein the first surface is disposed opposite the second surface;
   bonding the second plurality of elastomeric strands in a relaxed state along a second orientation to the first surface of the second nonwoven, wherein the first orientation is different from the second orientation;
   connecting the first surface of the first nonwoven with the first surface of the second nonwoven to form a laminate; and
   mechanically activating the second nonwoven of the laminate such that the second nonwoven is extensible along the machine direction.

2. The process of claim 1, further comprising the step of bonding a third plurality of elastomeric strands along a third orientation to the first surface of the first nonwoven, wherein the third orientation is different from the first orientation and the second orientation.

3. The process of claim 1, further comprising the step of applying adhesive to the first surface of the first nonwoven.

4. The process of claim 1, further comprising the step of applying adhesive to the first surface of the second nonwoven.

5. The process of claim 1, wherein the first orientation and the second orientation is a pre-determined angle from the machine direction.

6. The process of claim 1, wherein the step of mechanically activating further comprises meshing the second nonwoven between corrugated mating rolls.

7. The process of claim 1, wherein the second orientation of the second plurality of elastomeric strands is at least partially curvilinear.

8. A process for producing an elastomeric nonwoven laminate, the process comprising the steps of:
   advancing a nonwoven in a machine direction, the nonwoven having a first surface and second surface, wherein the first surface is disposed opposite the second surface;
   bonding a first plurality of elastomeric strands to a first portion of the first surface of the nonwoven along a first orientation, wherein the first orientation is parallel with the machine direction;

bonding a second plurality of elastomeric strands to a second portion of the first surface of the nonwoven along the first orientation;

bonding a third plurality of elastomeric strands to the first portion of the nonwoven along a second orientation, wherein the first orientation is different from the second orientation;

connecting the first portion of the first surface of the nonwoven with the second portion of the first surface of the second nonwoven.

9. The process of claim 8, further comprising the step of stretching the first plurality of elastomeric strands and the second plurality of strands in the machine direction.

10. The process of claim 9, wherein the first plurality of elastomeric strands and the second plurality of elastomeric strands are bonded in a stretched condition to the nonwoven.

11. The process of claim 10, wherein each of the first plurality of elastomeric strands and the second plurality of elastomeric strands is bonded to first surface of the nonwoven at bond points and is unbonded from the first surface between the bond points.

12. The process of claim 8, further comprising the step of folding the nonwoven to place the first portion of the first surface in a facing relationship with the second portion of the first surface.

13. The process of claim 8, further comprising the step of slitting the nonwoven.

14. The process of claim 8, further comprising the step of applying adhesive to the first surface of the first nonwoven.

15. The process of claim 8, wherein the first orientation and the second orientation is a pre-determined angle from the machine direction.

16. The process of claim 8, further comprising the step of mechanically activating the nonwoven.

17. The process of claim 8, wherein the second orientation of the third plurality of elastomeric strands is at least partially curvilinear.

* * * * *